United States Patent

Deshpande et al.

(10) Patent No.: US 7,741,477 B2
(45) Date of Patent: Jun. 22, 2010

(54) PROCESS FOR PURIFICATION OF SUCRALOSE

(75) Inventors: Pandurang Balwant Deshpande, Vadodara (IN); Parven Kumar Luthra, Vadodara (IN); Sanjiv Onkarsingh Tomer, Vadodara (IN); Piyush Maheshbhai Rana, Vadodara (IN); Jigar Kamleshbhai Patel, Vadodara (IN)

(73) Assignee: Alembic Limited, Gujarat (ID)

( * ) Notice: Subject to any disclaimer, the term of this patent is extended or adjusted under 35 U.S.C. 154(b) by 557 days.

(21) Appl. No.: 11/651,776

(22) Filed: Jan. 10, 2007

(65) Prior Publication Data

US 2007/0160732 A1 Jul. 12, 2007

(30) Foreign Application Priority Data

Jan. 10, 2006 (IN) .......................... 35/MUM/2006

(51) Int. Cl.
*C07H 1/00* (2006.01)
(52) U.S. Cl. ..................................... 536/124
(58) Field of Classification Search ........................ None
See application file for complete search history.

(56) References Cited

U.S. PATENT DOCUMENTS

| 4,362,869 A | 12/1982 | Jenner et al. |
| 4,380,476 A | 4/1983 | Mufti et al. |
| 4,783,526 A | 11/1988 | O'Brien et al. |
| 4,801,700 A | 1/1989 | Tully et al. |
| 4,977,254 A | 12/1990 | Homer et al. |
| 4,980,463 A | 12/1990 | Walkup et al. |
| 4,981,698 A * | 1/1991 | Cherukuri et al. ............... 426/5 |
| 5,034,551 A | 7/1991 | Vernon et al. |
| 5,141,860 A | 8/1992 | Bornemann et al. |
| 5,270,460 A | 12/1993 | Dordick et al. |
| 5,498,709 A | 3/1996 | Navia et al. |
| 6,809,198 B2 | 10/2004 | El Kabbani et al. |
| 2003/0171574 A1 | 9/2003 | Catani et al. |
| 2003/0171575 A1 * | 9/2003 | Catani et al. ................. 536/119 |

FOREIGN PATENT DOCUMENTS

| GB | 2 224 504 A | 5/1990 |
| WO | WO 2005/090374 A1 | 9/2005 |

* cited by examiner

*Primary Examiner*—Robert A Wax
*Assistant Examiner*—Jeffrey T Palenik
(74) *Attorney, Agent, or Firm*—Hamre, Schumann, Mueller & Larson, P.C.

(57) ABSTRACT

The present invention relates to a process for the purification of Sucralose of formula (I) which comprises acetylation of substantially impure Sucralose to its penultimate intermediate 4,1',6'-trichloro-4,1',6'-trideoxy galactosucrose penta-acetate (TOPSA) of formula (VI) followed by purification of TOPSA and then deacetylation of purified TOPSA.

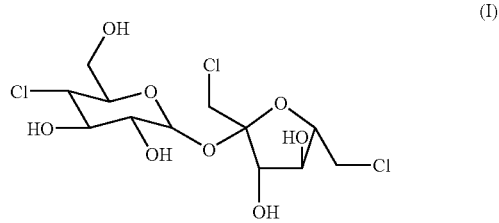

(I)

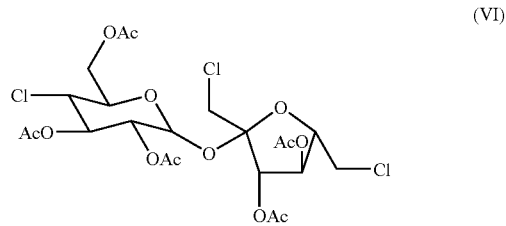

(VI)

2 Claims, No Drawings

PROCESS FOR PURIFICATION OF SUCRALOSE

FIELD OF INVENTION

The present invention relates to a process for the purification of Sucralose of formula (I) which comprises acetylation of substantially impure Sucralose to its penultimate intermediate 4,1',6'-trichloro-4,1',6'-trideoxy galactosucrose pentaacetate (TOPSA) of formula (VI) followed by purification of TOPSA and then deacetylation of purified TOPSA.

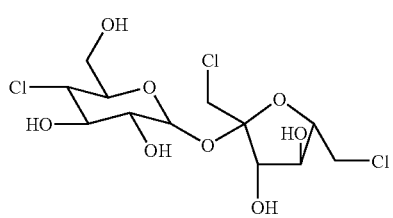

(I)

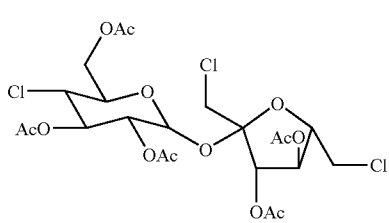

(VI)

BACKGROUND OF THE INVENTION

Sucralose is a potent sweetener having sweetness several hundred times that of sucrose. It is chemically known as 1,6-dichloro-1,6-dideoxy-β-D-fructofuranosyl-4-chloro-4-deoxy-α-galactopyranoside and having formula is $C_{12}H_{19}Cl_3O_8$ and molecular weight 397.64. Sucralose is used as sweetner in beverage, as coating tablet, chewing gum and other food products. It is marketed by McNeil under tradename Splenda®.

It is also chemically known as 4,1',6'-trichloro-4,1',6'-trideoxygalactosucrose, (hereinafter referred to as "Sucralose") involves the substitution of chlorine atoms in the sucrose molecule in one of the five secondary hydroxyl positions and in two of the three primary hydroxyl positions. This particular selection of positions usually means that any synthetic route must involve the preparation of an intermediate sucrose derivative having the required positions available for chlorination while the other positions are blocked. In particular, the reactive 6-position must not be chlorinated, while the 4-position must be rendered available for chlorination.

A process for preparing Sucralose is set forth in U.S. Pat. No. 4,362,869. This process converts sucrose through a number of steps into Sucralose. This process describes the sequential steps of (1) tritylation of sucrose to block the three primary alcohol groups; (2) acetylation of the five secondary alcohol groups as acetates; (3) detritylation of the three primary alcohol groups to deblock them; (4) acetyl migration from the 4-position to the 6-position; (5) chlorinating the desired alcohol groups at positions 4,1', 6'; and (6) deblocking the remaining five alcohol groups by deacetylation thereby yielding Sucralose.

The schematic representation is as given below (Scheme I)

Scheme (I)

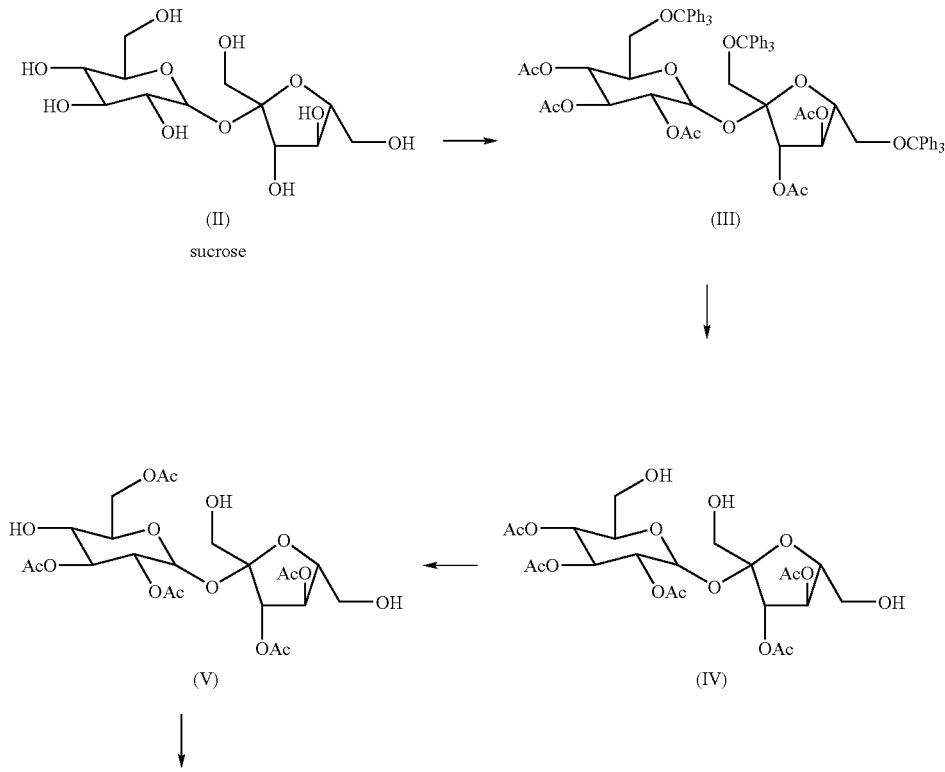

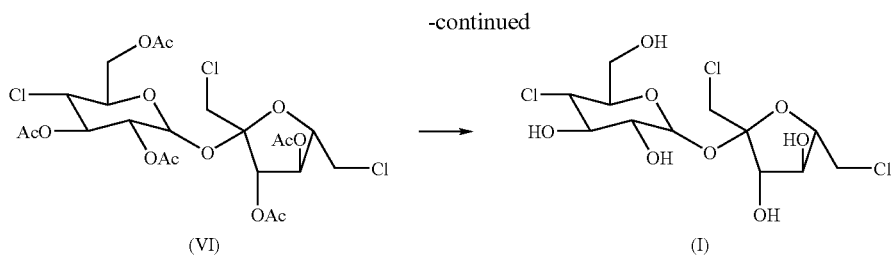

However, in this patent the purification of Sucralose is not mentioned.

U.S. Pat. No. 5,270,460 and WO2005090374 disclose the process of purification of Sucralose by silicagel chromatography or other chromatographic methods. However, purification of Sucralose by chromatographic method is commercially not feasible and cumbersome on large scale.

U.S. Pat. No. 4,801,700, U.S. Pat. No. 4,783,526, U.S. Pat. No. 5,141,860, U.S. Pat. No. 4,977,254 and GB2224504 disclose the process of purification of Sucralose by recrystallization from ethylacetate. This process provides Sucralose having some impurities which are difficult to remove even after repeated crystallization. Further, repeated crystallization would result in a loss of yield of the final product.

U.S. Pat. No. 4,380,476, U.S. Pat. No. 4,980,463 and U.S. Pat. No. 5,034,551 disclose the process of purification of Sucralose by crystallization from aqueous solution i.e. from water. However, there is substantial yield loss as Sucralose is highly soluble in water.

U.S. Pat. No. 5,498,709 and U.S. Application No. 20030171575 disclose the process of purification of Sucralose by crystallization from ethylacetate followed by recrystallization from water. This process also requires repeated purification from different kind of solvents which may result in low yield.

U.S. Pat. No. 6,809,198 discloses the process of purification of Sucralose by cystallization from aqueous solution in controlled pH condition at pH 5.5 to 8.5 using buffer solution. This process requires regular monitoring of pH. It also requires special kind of industrial apparatus for the purification process. These drawbacks make the process cumbersome at an industrial scale.

U.S. Application No. 20030171574 discloses the process of purification of Sucralose by extractive method which involves repeated extraction from first solvent (i.e. water), second solvent (i.e. ethylacetate) and third solvent (i.e. ethylacetate).

This process also requires special kind of industrial apparatus to perform the purification. Moreover, this kind of process which requires repeated extraction is tedious and laborious to perform.

It is therefore, there is a need to develop a process for purification of Sucralose which not only overcomes the aforementioned problems but also provide a process which is simple, easy to handle and feasible at commercial production.

The final Sucralose is always contaminated with several unwanted polar impurities because of the nature of product which contains three hydroxy groups having similar solubility. These impurities can not be removed by repeated recrystallization of Sucralose even using different solvents. The present inventors have directed their research work towards developing a new process for purification of Sucralose which provides highly pure Sucralose without repeated recrystallization of substantially impure Sucralose.

Surprisingly, the present inventors have found that by converting substantially impure Sucralose to its penultimate intermediate i.e. TOPSA and then crystallizing it from an organic solvent significantly removes the impurities which were present in Sucralose. After purifying TOPSA, it can be converted to Sucralose by deacetylation. Unexpectedly the Sucralose obtained by this method is highly pure.

OBJECT OF THE INVENTION

A primary object of the present invention is to provide a process for the purification of substantially impure Sucralose.

Another object of the present invention is to provide a process for the purification of substantially impure Sucralose without performing repeated recrystallization, which is cumbersome on industrial scale.

Another object of the present invention is to provide a process for the preparation of Sucralose which provide Sucralose with improved purity.

Yet another object of the present invention is to provide an improved a process for the preparation of Sucralose, which is simple, easy to handle and feasible at commercial scale.

SUMMARY OF THE INVENTION

Accordingly, present invention provides a process for the purification of substantially impure Sucralose to obtain sucralose having at least 99% purity, said process comprising steps of:

(i) converting substantially impure Sucralose to its penultimate 4,1',6'-trichloro-4,1',6'-trideoxy galactosucrose penta-acetate (TOPSA) by acylation;

(ii) purifying the TOPSA obtained in above step (i);

(iii) converting TOPSA obtained in above step (ii) to Sucralose by deacylation

DETAILED DESCRIPTION OF THE INVENTION

Accordingly, present invention provides a process for the purification of substantially impure Sucralose to obtain sucralose having at least 99% purity, said process comprising steps of:

(i) converting substantially impure Sucralose to its penultimate 4,1',6'-trichloro-4,1',6'-trideoxy galactosucrose penta-acetate (TOPSA) by acylation;

(ii) purifying the TOPSA obtained in above step (i);
(iii) converting TOPSA obtained in above step (ii) to Sucralose by deacylation.

For the purpose of this specification, the meaning of the phrase "substantially impure" used in this specification is Sucralose having purity less than 99.0%

Conversion of impure Sucralose to TOPSA is carried out in the presence of acylating reagent, base and suitable aprotic solvent at ambient temperature for period of time sufficient to complete acylation.

The acylating reagent used may be any acylating reagent which will produce an ester of Sucralose. In general, a reagent serving to form an aliphatic, araliphatic or aryl carboxylate is suitable. Particularly suitable carboxylates include lower alkyl carboxylates such as acetates and propionates; and aryl carboxylates such as benzoates. The acylating reagent may be any active derivative of the relevant acid, and in the case of carboxylic acylation is preferably an acyl anhydride or acyl halide. Other reagents include enyl acylates or other suitably active esters.

The reaction conditions for the acylation will, of course, depend on the nature of the acylating reagent. Reaction of sucrose with a carboxylic anhydride, such as acetic anhydride, is conveniently effected in the presence of a base, particularly a basic tertiary amine solvent, such as pyridine. Reaction with an acyl halide may be effected under similar conditions to the reaction with an anhydride, or alternatively may utilize aqueous alkaline conditions (e.g. the well-known Schotten-Baumann conditions).

The examples of anhydrides mentioned hereinabove include but not limited to acetic anhydride, benzoic anhydride and the like or mixture thereof. The examples of acylhalides mentioned hereinabove include but not limited to acetyl chloride, benzoyl chloride, and the like or mixture thereof.

The base mentioned hereinabove is selected from the group comprising of tertiary amine base and inorganic base. The examples of tertiary amine base mentioned hereinabove include but not limited to pyridine, collidine, 2,4,6 trimethylpyridine, N-methylpyrrolidone, lutidine and the like or mixture thereof. The examples of inorganic base mentioned hereinabove include but not limited to sodium acetate, potassium acetate and the like or mixture thereof.

The suitable aprotic solvent mentioned hereinabove is selected from the group comprising of aromatic hydrocarbon, chlorinated hydrocarbon and ester. The examples of aromatic hydrocarbon include but not limited to toluene, xylene, benzene and the like or mixture thereof. The examples of chlorinated hydrocarbon include but not limited to dichloromethane, dichloroethane, chloroform, carbon tetrachloride and the like or mixture thereof. The examples of ester include but not limited to ethylacetate and the like or mixture thereof.

After completion of the reaction, the mass is washed with 10% HCl solution followed by D.M. water. The organic layer is separated and evaporated to give crude TOPSA.

Purification of TOPSA is done by recrystallizing TOPSA from various organic solvent. The examples of organic solvent mentioned hereinabove include but not limited to methanol, ethanol, ethylacetate, acetone and the like or mixture thereof.

The purification of TOPSA can be achieved by other methods such as solvent/antisolvent treatment or trituration with partial miscible solvent. Any purification process for purification of TOPSA is included within the scope of this invention.

The crude product TOPSA is dissolved in an organic solvent at elevated temperature preferably at reflux. The solution is cooled first at ambient temperature and then at −15 to 5° C. to precipitate out the product. The product is filtered, optionally washed with the same solvent and dried at 40-50° C. to get pure TOPSA.

The deacetylation of TOPSA is done by methods known perse or by any method known to person skilled in art using alkoxide in alcohol.

Sucralose obtained by performing purification mentioned in this application is having purity more than 99.0%

The process of the present invention is described by the following examples, which are illustrative only and should not be construed so as to limit the scope of the invention in any manner.

Example 1

(a) Preparation of TOPSA from Impure Sucralose

Sucralose (330 g) was added to a mixture of acetic anhydride (783.3 ml), pyridine (33 ml) and dichloromethane (990 ml) and stirred at ambient temperature for 4-5 hours. The reaction was monitored on TLC. The mass was washed twice with 10% HCl solution (825 ml) and then with D.M water (1650 ml). Organic layer was separated and evaporated to give residue (520 gm)

(b) Purification of TOPSA

TOPSA obtained in above step (a) was dissolved in methanol (2020 ml) at reflux temperature and stirred for 20 min. The mass was cooled first at ambient temperature and then chilled to −6 to 0° C. The solid precipitate out was filtered, washed with chilled methanol and dried at 40° C. under reduced pressure to give the pure TOPSA (468 g).

(c) Preparation of Sucralose from TOPSA

Pure TOPSA (462 g) obtained in above step (b) was dissolved in methanol and stirred for complete dissolution. A solution of sodium methoxide in methanol (44 ml) was added dropwise till pH of solution 10.5 was obtained. The mass was neutralized by adding $H^+$ cation resin (30 g) and then filtered. The filtrate was charcoalized and then on evaporation of solvent gave pure Sucralose (313.8 g). This product can optionally be purified by crystallizing from ethylacetate. The purity of the sucralose obtained is more than 99.4% (by HPLC).

The invention claimed is:
1. A process for purification of substantially impure Sucralose of formula (I) to obtain sucralose having at least 99% purity, said process comprising steps of:

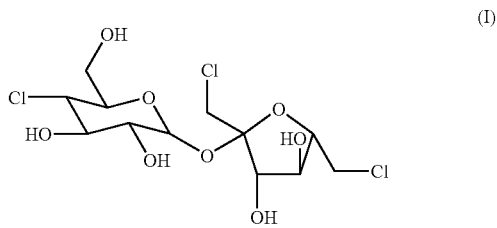

(i) converting substantially impure Sucralose to its penultimate 4,1',6'-trichloro-4,1',6'-trideoxy galactosucrose pentaacetate (TOPSA) of formula (VI) by acetylation;

wherein the step (i) acetylation is carried out in the presence of acetic anhydride, pyridine and dichloromethane;

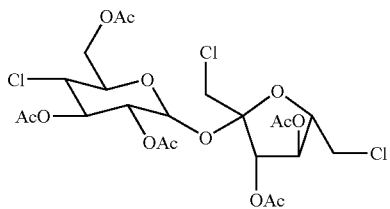

(VI)

(ii) purifying the TOPSA obtained in above step (i);

wherein the step (ii) purification is carried out as a single round of crystallization from methanol; and (iii) converting TOPSA obtained in above step (ii) to Sucralose by deacetylation.

2. The process as claimed in claim 1, wherein the step (iii) deacetylation is carried out in the presence of sodium methoxide in methanol.

* * * * *